United States Patent [19]

Johnson et al.

[11] Patent Number: 4,518,534

[45] Date of Patent: May 21, 1985

[54] LAYERED VANADIUM COMPOUNDS CONTAINING PHOSPHORUS OR ARSENIC AND PENDANT ORGANIC GROUPS

[75] Inventors: Jack W. Johnson, Clinton; Allan J. Jacobson, Princeton, both of N.J.

[73] Assignee: Exxon Research and Engineering Co., Florham Park, N.J.

[21] Appl. No.: 525,142

[22] Filed: Aug. 22, 1983

[51] Int. Cl.$^3$ .......................... C07F 9/00; C07F 9/38; C07F 9/70; C07F 9/09

[52] U.S. Cl. .................... 260/429 R; 528/395; 528/398; 528/9; 528/223; 528/224; 528/271; 528/287; 528/362; 528/374; 528/373

[58] Field of Search ................. 260/429 R, 429 J; 528/395, 9, 30, 222, 223, 224, 362, 374, 391, 392, 271, 398, 287, 373

[56] References Cited

U.S. PATENT DOCUMENTS

| | | |
|---|---|---|
| 4,351,735 | 9/1982 | Buddemeyer et al. ......... 260/429 R |
| 4,386,013 | 5/1983 | Callahan et al. ............... 260/429 R |
| 4,390,690 | 6/1983 | DiGiacomo et al. .......... 260/429 R |
| 4,429,111 | 1/1984 | Dines et al. .................... 260/429 R |
| 4,436,899 | 3/1984 | DiGiacomo et al. .......... 260/429 R |

OTHER PUBLICATIONS

Dines et al., *J. Phys. Chem.*, 86, 571 (1982).
Alberti et al., *J. Inorg. Nucl. Chem.*, 40, 1113 (1978).

*Primary Examiner*—Helen M. S. Sneed
*Attorney, Agent, or Firm*—Edward M. Corcoran

[57] ABSTRACT

A layered oxide containing vanadium together with phosphorus or arsenic and an organic group may be prepared which has a unique layered structure of the formula: $VORAO_3 \cdot nS$ or $VOROAO_3 \cdot nS$ where A is phosphorus or arsenic, S is a solvent molecule, R is an unsubstituted or alkyl-, alkoxy- or aryl-substituted alkyl or aryl group, and n is zero or a positive number. These layered compounds are characterized in that the vanadium is substantially in a 4+ oxidation state and is present in an amount such that the molar ratio of A:V ranges from 0.8 to 1.2 throughout the oxide. Also the R groups are covalently bound to an A atom in the vanadium oxide layer directly through either carbon or oxygen atoms.

18 Claims, 5 Drawing Figures

FIG. 5
LAYERED VANADIUM COMPOUNDS CONTAINING PHOSPHORUS OR ARSENIC AND PENDANT ORGANIC GROUPS

BACKGROUND OF THE INVENTION

This invention relates to a novel composition of matter composed of layered oxides containing vanadium together with phosphorus or arsenic wherein monovalent organic groups (R) are covalently bound to the phosphorus or arsenic atoms within the layered oxide structure. Typically R is bound directly through carbon or through an oxygen bridge. In the former case the compounds are phosphonates or arsonates whereas in the latter case they are phosphates or arsenates.

The open and patented literature discloses layered phosphonates and/or phosphate compounds of the formula $M(O_3PR)_2$ or $M(O_3POR)_2$ wherein the pendant organic R groups on the phosphorus atoms are directed toward the interlayer space. See, for example, Dines et al., *Inorg. Chem.*, 22, 567 (1983) (Th phosphonates), *Polyhedron*, 1, 61 (1982) (Zr phosphonates), *Inorg. Chem.*, 20, 92 (1981) (Zr, Th, Ti, Ce and U phosphonates and phosphates), and *J. Phys. Chem.*, 86, 571 (1982) (Zr phosphonates), Alberti et al., *J. Inorg. Nucl. Chem.*, 40, 1113 (1978) (Zr phosphonates and phosphates), and U.S. Pat. Nos. 4,232,146; 4,235,990; and 4,256,872. (Zr compounds). Other patents directed to layered organoarsenous or organophosphorus inorganic polymers include U.S. Pat. Nos. 4,374,242; 4,276,410; 4,276,411; 4,298,723; 4,299,943; 4,373,079; 4,235,991; and 4,267,308.

While these references and others teach formation of layered structures by reacting organophosphorus compounds with tetravalent metal salts, the complexes formed have a metal to phosphorus ratio of 1:2 and the references do not suggest use of vanadium as a tetravalent metal.

U.S. Pat. Nos. 4,376,709 and 4,355,162 disclose compositions containing a layered mixed oxide having layers of corner-linked octahedra and tetrahedra including $VOPO_4$ (V in a 5+ oxidation state) which may be intercalated with a cation or reacted with a nitrogen donor Lewis base covalently bonded to the vanadium. U.S. Pat. No. 4,237,061 discloses formation of intercalates of organometallic compounds by reacting with a tetravalent cation metal salt of an organic phosphate, arsenate or vanadate. The cation is not vanadium and the compound was a cation to anion ratio of 1:2.

SUMMARY OF THE INVENTION

In accordance with the present invention there is disclosed a solid composition of matter comprising layered oxides containing vanadium together with phosphorus or arsenic and a monovalent organic group, said layered compounds having one of the formulae:

$VORAO_3.nS$ or $VOROAO_3.nS$ where A is phosphorus or arsenic, S is a solvent molecule, R is an unsubstituted alkyl or aryl group or an alkyl-, alkoxy- or arylsubstituted alkyl or aryl group or a mixture thereof, and n is zero or a positive number, preferably from 0 to 10, the layered compounds being characterized in that the vanadium has an average oxidation state in the range of 3.6 to 4.4 and is present in an amount such that the molar ratio of A:V ranges from 0.8 to 1.2 throughout the oxide and the R groups are covalently bound to an A atom in the vanadium oxide layer directly through either carbon or oxygen.

The layered compositions herein thus contain pendant alkyl, aralkyl or aryl groups covalently bonded to the phosphorus or arsenic atom contained in either side of the layer. The organic groups (R) are oriented in a direction toward the space between the layers. Additionally, reactive groups may be incorporated into the R group such as $-NH_2$, $-OH$, and $-PR_2$ so that various catalytically active metals can be coordinated to the compound between the layers. The compounds herein are useful by themselves as solid sorbents in selective separations of various compounds and also find use as oxidation catalysts or as catalysts in hydrocarbon conversion or synthesis reactions when a catalytically active metal is intercalated into the layered compound containing the reactive groups.

While the literature discloses various layered metal organophosphonates and organophosphates, these compounds have a phosphorus to metal molar ratio of 2.0, rather than the 0.8 to 1.2 ratio of the present invention, so that the detailed structures of the publicly disclosed compounds are different.

DESCRIPTION OF THE PREFERRED EMBODIMENTS

Figure 2:
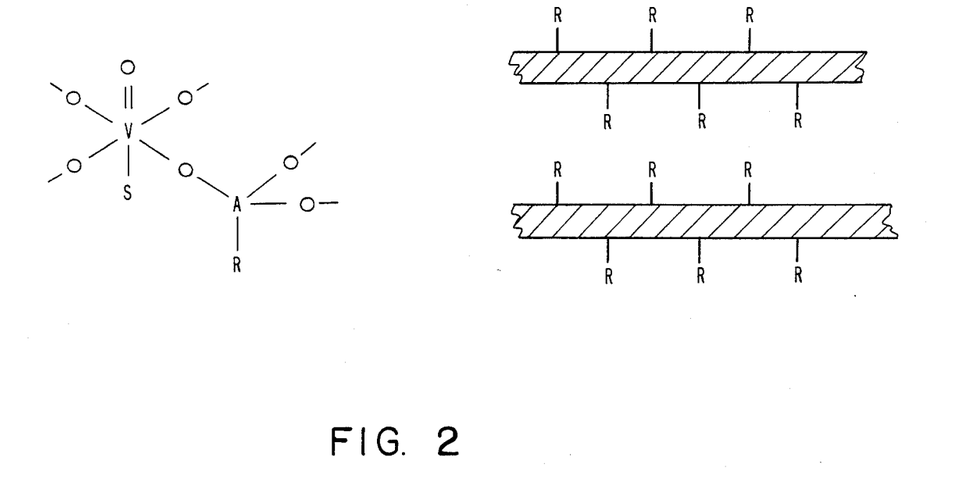
FIG. 2 illustrates a schematic diagram of the bonding arrangement of the $VO(RAO_3).nS$ (arsonate or phosphonate) compounds, including a cross-sectional view of the layers.
Figure 3:
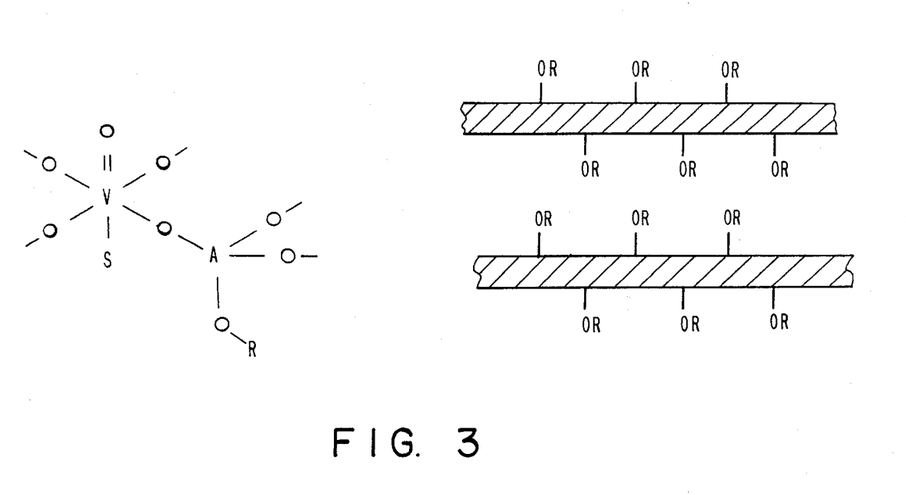
FIG. 3 illustrates a schematic diagram of the bonding arrangement of the $VO(ROAO_3).nS$ (arsenate or phosphate) compounds, including a cross-sectional view of the layers.

The compounds of the invention comprise vanadium-phosphorus or vanadium-arsenic oxide layers which have a monovalent organic group inserted between the oxide layers and directly bound to the phosphorus or arsenic atom. The organic group can be covalently bonded directly through carbon to produce phosphonates and arsonates or through oxygen to yield phosphates and arsenates. Coupling of the organic group to the phosphorus or arsenic atoms may also be achieved through an intermediate atom such as silicon, sulfur, nitrogen and the like. Unlike layered vanadium oxides containing organic groups described in U.S. Pat. Nos. 4,376,709 and 4,355,162, the compounds herein have vanadium in a +4 oxidation state which is not coordinated to the organic groups. FIGS. 2 and 3 illustrate the unique physical structure of the two types of compounds where the cross-hatched sections represent the layers of oxygen, vanadium and arsenic or phosphorus from which the organic groups (R or OR) are pendant in both directions.

The R groups attachable to phosphorus or arsenic atoms in the vanadium oxide layer of the presently disclosed compounds include, but are not limited to, alkyl, alkenyl, alkynyl, haloalkyl, arylalkyl, mercaptoalkyl, aminoalkyl, carboxyalkyl, cyanoalkyl, sulfoalkyl, alkoxyalkyl, aryloxyalkyl, diketoalkyl, aryl, haloaryl, alkylaryl, aminoaryl, mercaptoaryl, carboxyaryl, cyanoaryl, sulfoaryl, alkoxyaryl, aryloxyaryl, diketoaryl or mixtures thereof. More preferably, the organic group is a phenyl, biphenyl, $C_1$-$C_4$-alkyl- or $C_1$-$C_4$-alkoxy-substituted phenyl, $C_1$-$C_{20}$ alkyl group, or mixtures thereof. Examples of these monovalent organic groups include p-methoxyphenyl, p-ethoxyphenyl, ethyl, methyl, propyl, hexyl, octyl, decyl, octadecyl, naphthyl and the like. These groups may optionally include pendant functional groups containing, e.g., oxygen, sulfur, nitrogen, phosphorus, halogen or other atoms, which groups are reactive with transition metals. Preferred among such groups are —COOR, —$NH_2$, —OH, —$PR_2$, —CN, —COOH, —SH, —$SO_3H$, and more preferred are —COOR, —COOH, —OH and —CN. If the organic group contains such functional groups it will coordinate, between the oxide layers, metals such as Ni(+2), Ru(+2), Fe(+2) and other metals which are catalytically active so as to produce an intercalated structure useful as a catalyst in, for example, hydrocarbon conversion reactions. Specific examples of suitable organic groups for this purpose include aminophenyl, —$CH_2COOH$, —$CH_2CH_2SH$, chloromethyl, dimethylphosphinoethyl, cyanoethyl, hydroxymethyl, hydroxyethyl, aminoethyl, bromophenyl, and other groups. Mixtures of R groups containing such functional groups may also be employed.

It is to be noted that the layered oxides of this invention may contain more than one type of organic (R) group. In addition, the oxides may be composed of mixed organophosphates/phosphonates or mixed organoarsenates/arsonates or other combinations of these groups depending on the mixture of reagents employed and the ultimate use desired. Such mixtures may be important in increasing the microporosity of the oxide compounds.

The layered compounds herein are characterized by the vanadium having an average oxidation state in the range of 3.6 to 4.4. In the most preferred embodiment the vanadium oxidation state is in the range of 3.9 to 4.1. In addition, the vanadium must be present in an amount such that the molar ratio of P:V or As:V ranges from 0.8 to 1.2 throughout the compound. This feature clearly distinguishes the present compounds from those of the prior publications wherein comparable ratios are 2.0.

The compounds of this invention may also have incorporated therein one or more solvent molecules which depend on the particular method of preparation or the solvent used to wash the compound. The compounds, however, need not contain any solvent. Preferably the number of solvent molecules incorporated in the compound is 0 to 10.

Figure 1:
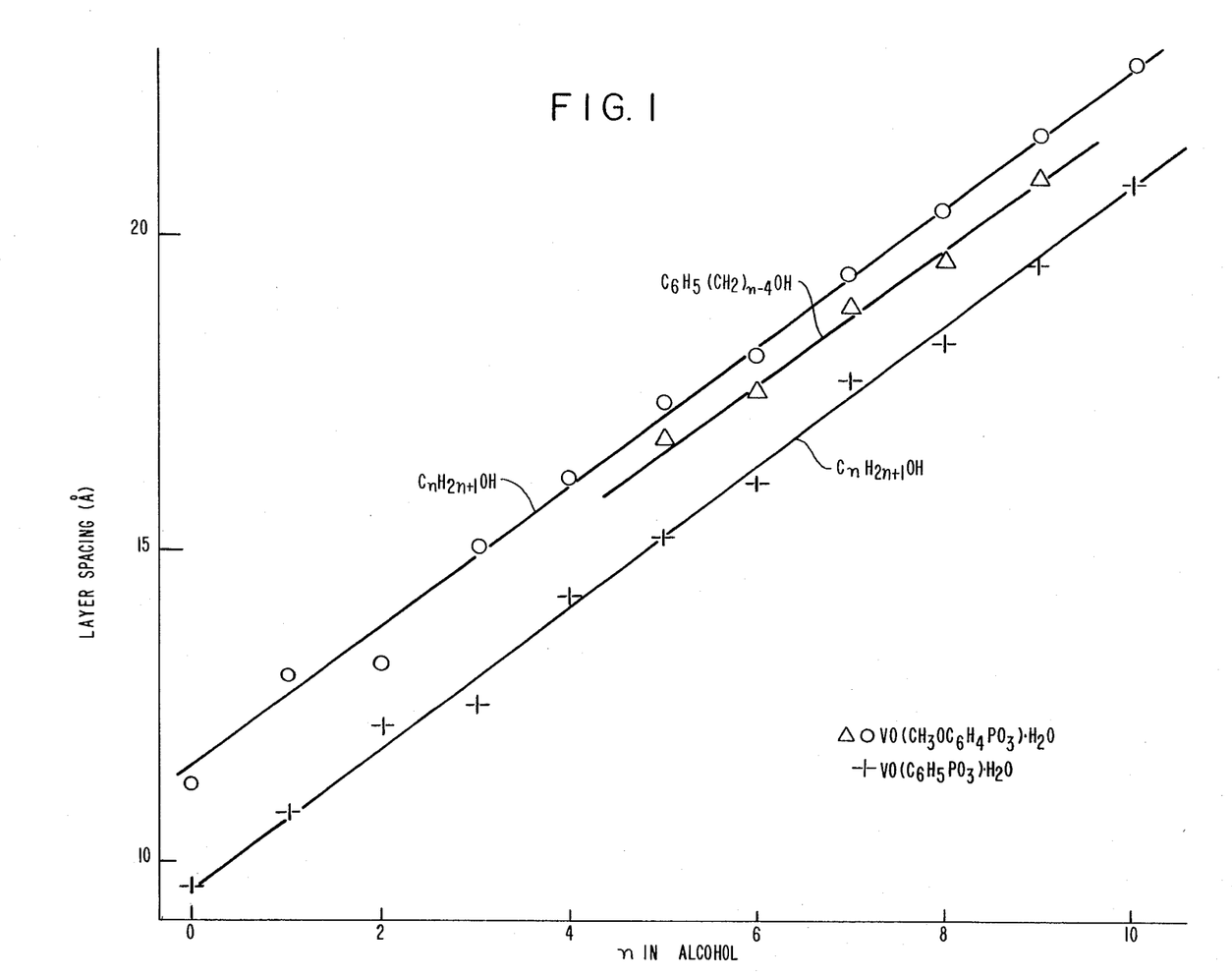
FIG. 1 illustrates a plot of the interlayer spacing of two compounds of this invention, $VO(CH_3OC_6H_4PO_3).H_2O$ and $VO(C_6H_5PO_3).H_2O$, in various alcohol solvents S, as a function of the chain length of the alcohol.

In one preferred embodiment the solvent molecule is a $C_1$-$C_{20}$ aliphatic or aromatic alcohol. FIG. 1 illustrates a plot of layer spacing in two phosphonate compounds as a function of the value of n in $C_nH_{2n+1}OH$ and $C_6H_5(CH_2)_{n-4}OH$ when they are used as solvents. It can be seen that the layer spacing increases as the chain length of the alcohol increases, and thus that the compounds herein will expand as they intercalate molecules in sorption separations. The optimum layer spacing for the compounds herein will depend mainly on the desired ultimate separation or catalyst use of the compound. Preferably this layer spacing will range from about 8 to 80 Å, and more preferably from about 8 to 48 Å. The layer spacing is dependent not only on the solvent, but also to varying degrees on the type of organic group employed, whether the compound is a phosphonate or phosphate, and whether phosphorus or arsenic is employed.

Other solvents which may be incorporated in these layered compounds besides alcohols include water, ethers, hydrocarbons, amides, amines, esters, ketones, and the like, or mixtures thereof.

The composition of matter of this invention may be prepared by several methods. Any suitable reaction vessel equipped with a heating means may be employed such as a round-bottomed flask equipped with an electric heating mantle, a magnetic stirrer, and a reflux condenser. In one such method a vanadium 5+ compound such as, e.g., vanadium pentoxide or vanadyl chloride is contacted with an effective amount, i.e., from at least equimolar to a large excess over the equimolar amount of a phosphonic, phosphoric, arsonic or arsenic acid of the organic group as described above (which may also be referred to as R-substituted phosphonic, phosphoric, arsonic or arsenic acid), in the presence of a solvent and, if the solvent does not function as a reducing agent, a reducing agent. The particular acid employed will depend on the compound ultimately desired. For example, use of an organophosphonic acid will result in a vanadium organophosphonate, whereas use of an organophosphoric acid will result in a vanadium organophosphate. Employing oxides substituted with different R groups or employing mixtures of, e.g., phosphonic and phosphoric acids will result in mixed compounds as described above. Examples of solvents vents which function as reducing agents for the vanadium (5+) include alcohols such as ethanol, isopropanol, iso-or secondary butanol, and the like, most preferably ethanol. If the solvent acts as a reducing agent it is employed in an excess over the amount necessary for reduction. If the solvent does not act as a reducing agent, an agent for reduction of the vanadium (5+) cation must be present in the mixture. Examples of suitable reducing agents for this purpose include $SO_2$ and hydroquinone.

In the alternative method for preparing the compositions of this invention a vanadium 4+ compound such as, e.g., vanadyl sulfate or vanadyl acetylacetonate is contacted directly with an effective amount (as defined above) of the R-substituted acid as defined above in a suitable solvent. The solvent is preferably an alcohol since all the reactants are soluble therein, but other solvents which have adequate boiling points to ensure attainment of a sufficient reaction temperature and which adequately dissolve the reactants may be employed.

In both methods of preparation, after the vanadium compound is contacted with the R-substituted acid, the resultant mixture is heated at temperatures which depend mainly on the particular reactants employed but generally range from about 50° C. to the reflux temperature of the reaction medium for a period of time sufficient to detect the product in isolable amounts. Preferably the reaction temperature is the reflux temperature if ethanol is employed as the solvent.

After the product is detected it is recovered from the reaction medium by any suitable techniques. Where an alcohol is employed as solvent the product is preferably recovered by cooling and filtering the reaction mixture and then washing and drying the product.

The compounds herein may be used in hydrocarbon oxidation reactions such as, for example, oxidation of butane to maleic anhydride, wherein the catalyst is contacted with the hydrocarbon substrate during the oxidation reaction under catalytic conditions by methods known to those skilled in the art. They may also be used as supports for incorporation of catalytically active metal centers if they contain reactive organic groups as discussed above. In addition, the compounds may be employed as solid sorbents for the selective separation of various organic compounds. For example, the compound herein may be contacted with a mixture of chloroform, benzene and 1-hexanol under conditions so that the compound absorbs the components of the mixture. Thereafter, the components may be selectively desorbed from the compound under desorption conditions using a suitable desorbent therefor. One possible application for the solid sorbent is in gas-solid chromatography using the compound of this invention in the chromatography column.

The examples which follow illustrate the efficacy of the invention. In the examples, all parts and percentages are given in weight unless otherwise noted and n in the formulae is zero or a positive number.

EXAMPLE 1

A mixture of 1 g of vanadium pentoxide and 1.74 g of phenylphosphonic acid in 60 ml of 95% ethanol (serving as both reducing agent and solvent) was refluxed for 114 hours in a round-bottomed flask equipped with a stirrer, electric heating mantle and condenser. During this period the suspended solid in the mixture changed from orange to blue, indicating reduction of $V^{5+}$ to $V^{4+}$. The reaction mixture was thereafter cooled to room temperature, filtered and washed twice with ethanol. The final product was dried at 68° C. in vacuum for 15 hours. An X-ray power diffraction pattern of the product indicated a layered vanadium phosphonate compound with a layer separation of 12.6 Å. The product had the formula:

$VO(C_6H_5PO_3).nS$ where S is ethanol or water or mixtures of water and ethanol.

EXAMPLE 2

A mixture of 2.6 g of vanadyl sulfate ($VOSO_4.3H_2O$) and 3.8 g of phenylphosphonic acid in 60 ml of 95% ethanol was refluxed for 5 days (120 hours) as described in Example 1. The reaction mixture was thereafter cooled to room temperature and the bright blue solid obtained was filtered and washed well with ethanol. The final product was dried under vacuum at room temperature for 15 hours. An X-ray pattern of the product indicated a layered compound with a layer-to-layer separation of 12.6 Å similar to that obtained by the procedure of Example 1. The product had the same formula as the product of Example 1.

EXAMPLE 3

A mixture of 1.26 g vanadyl acetylacetonate ($VO(C_5H_7O_2)_2$) and 0.75 g phenylphosphonic acid in 60 ml 95% ethanol was refluxed and stirred for 5 hours. The blue solid formed was separated by filtration and washed with ethanol. X-ray powder diffraction showed the product to be identical with $VO(C_6H_5PO_3).nS$ prepared in Examples 1 and 2.

EXAMPLE 4

A mixture of 1 g of vanadium pentoxide and 3.1 g of p-methoxyphenylphosphonic acid in 60 ml of 95% ethanol was refluxed for 11 days as described in Example 1. During this time the solids in the suspended mixture changed from orange to blue-green, indicating reduction of $V^{5+}$ to $V^{4+}$. The reaction mixture was then cooled to room temperature, and the solid was filtered and washed with ethanol. The final product was dried under vacuum for 15 hours. An X-ray powder diffraction pattern indicated an interlayer separation of 13.24 Å. The product obtained had the formula:

$VO(p\text{-}CH_3OC_6H_5PO_3).nS$ where S is ethanol, water or mixture of water and ethanol.

EXAMPLE 5

A mixture of 1.3 g of vanadium pentoxide and 5 g 4-biphenylphosphonic acid ($C_{12}H_9PO(OH)_2$) was refluxed in 175 ml of 95% ethanol for five days as described in Example 1. The light blue solid produced thereby was filtered, washed with 95% ethanol and dried under vacuum at room temperature. The reaction was quantitative based on vanadium. The product was then washed with water at 55° C. for 24 hours and then dried under vacuum at 75° C. An X-ray diffraction powder pattern revealed the product as crystalline and single phase with orthorhombic cell constants of a=9.96, b=13.95 and c=9.79 Å, where the b axis corresponds to the layer to layer separation. Elemental analysis revealed a composition of 43.03%C, 3.91%H, 9.32%P and 15.11% V as compared with the theoretical values of 43.01%C, 3.91%H, 9.24%P and 15.20% V, calculated for $VO(C_{12}H_9PO_3).2H_2O$.

EXAMPLE 6

A mixture of 0.5 g of vanadium pentoxide, 0.78 g of 4-biphenylphosphonic acid and 0.48 g of phenyl phosphonic acid was refluxed in 150 ml of 95% ethanol for 7 days. The light blue solid product resulting therefrom was filtered, washed with 95% ethanol and vacuum dried. The yield based on vanadium was 82% by weight. The product was then washed by stirring in water at 60° C. for 19 hours, filtered and dried at 66° C. under vacuum. An X-ray diffraction powder pattern of the product yielded a single phase with a b axis of 14.00 Å similar to that observed for the pure biphenyl compound (13.95 Å). The reaction yield indicates that the compound contains both phenyl and biphenyl phosphonate groups, but the similarity to the pure biphenyl compound interlayer spacing indicates that biphenyl determines the layer separation. Consequently, additional porosity is introduced near the phenyl groups. The product had the formula:

$VO(C_{12}H_9PO_3)_x(C_6H_5PO_3)_{1-x}.nS$ where S is ethanol, water or mixtures of water and ethanol.

EXAMPLE 7

A mixture of 1 g of vanadium pentoxide and 1.07 g of methylphosphonic acid was refluxed in 60 ml of 95% ethanol as described in Example 1. After 20 hours some color change could be observed but the reaction appeared to be slow. An additional 0.5 g of methylphosphonic acid was added to increase the P:V ratio from 1:1 to 1.5:1 in the reactant mixture. The rate of reaction increased when the additional methylphosphonic acid was added, and after a further 22 hours all of the solid suspended in the mixture was blue. The reaction mixture was cooled to room temperature, and the solid was filtered, washed with ethanol, and dried under vacuum for 24 hours. An X-ray powder diffraction pattern showed a layer-to-layer separation of 9.6 Å. The product obtained had the formula:

$$VO(CH_3PO_3) \cdot nS$$

where S is ethanol, water or mixtures of water and ethanol.

EXAMPLE 8

A mixture of 1 g of vanadium pentoxide and 1.84 g of ethylphosphonic acid was refluxed in 60 ml of 95% ethanol for 5 days as described in Example 1. The solids suspended in the mixture changed from orange to light blue during this time indicating reduction of $V^{5+}$ to $V^{4+}$. The reaction mixture was then cooled to room temperature and the solid was filtered, washed with ethanol and dried under vacuum at room temperature for 16 hours. An X-ray powder diffraction pattern indicated a layer-to-layer separation of 11.1 Å. The product obtained had the formula:

$$VO(CH_3CH_2PO_3) \cdot nS$$

where S is ethanol, water or mixture of water and ethanol.

EXAMPLE 9

A mixture of 0.9 g vanadium pentoxide and 5 g octadecyl phosphonic acid ($C_{18}H_{37}PO(OH)_2$) was refluxed in 160 ml of 95% ethanol for 14 days. The blue solid product obtained was filtered, washed with 95% ethanol and dried under vacuum. An X-ray powder pattern of the product revealed that it contains two layered compounds with interlayer separations of 44.6 and 41.8 Å. The 41.8 Å phase is a minor component. The product obtained had the formula:

$$VO(C_{18}H_{37}PO_3) \cdot nS$$

where S is ethanol, water or mixtures of water and ethanol. The different spacings are to be associated with different values of n.

EXAMPLE 10

A mixture of 0.53 g of vanadium pentoxide and 1.4 g hydroxymethylphosphonic acid ($HOCH_2PO(OH)_2$) was refluxed in 30 ml of 95% ethanol for three days as described in Example 1. The yellow vanadium pentoxide was converted to a blue product as the reaction proceeded. The solid product was filtered, washed with ethanol and dried under vacuum. An X-ray powder diffraction pattern of the product indicated a layer-to-layer separation of 8.8 Å. The product obtained had the formula:

$$VO(HOCH_2PO_3) \cdot nS$$

where S is ethanol, water or mixtures of water and ethanol.

This example illustrates formation of a composition containing a pendant organic functional group (OH).

EXAMPLE 11

A mixture of 1.05 g of vanadium pentoxide and 1.81 g of phosphonacetic acid ($HOOCCH_2PO(OH)_2$) was refluxed in 60 ml of 95% ethanol for three days as described in Example 1. The light blue solid produced thereby was filtered, washed with ethanol and dried under vacuum at room temperature. An X-ray powder diffraction pattern of the product indicated a layer-to-layer separation of 8.6 Å. The product obtained had the formula:

$$VO(HOOCCH_2PO_3) \cdot nS$$

where S is ethanol, water, or mixtures of water and ethanol.

This example illustrates formation of another composition containing a pendant organic functional group (COOH).

EXAMPLE 12

A mixture of 1.2 g vanadium pentoxide and 0.66 g of the ethyl ester of phosphonoacetic acid ($C_2H_5OOCCH_2PO(OH)_2$) was refluxed in 75 ml of absolute ethanol for three days. The light blue-green solid product resulting therefrom was filtered, washed with absolute ethanol and dried under vacuum. An X-ray powder diffraction pattern indicated that the product was single phase with an interlayer separation of 9.6 Å. The product obtained had the formula:

$$VO(C_2H_5OOCCH_2PO_3) \cdot nS$$

where S is ethanol, water or mixtures of ethanol and water.

This example illustrates another compound containing a pendant organic functional group (COOC$_2$H$_5$).

EXAMPLE 13

A total of 3.9 ml concentrated HCl was added to a suspension of 6.27 g of sodium phenylphosphate in 100 ml of 95% ethanol. The mixture was stirred overnight and 2.73 g sodium chloride was separated by filtration, as determined by X-ray diffraction analysis. A total of 2.00 g of finely ground vanadium pentoxide was added to the resulting solution of phenylphosphoric acid and the mixture was refluxed with stirring for five days. After this time, the suspension was yellow-green. Another portion of phenylphosphoric acid (made from 6.27 g of $C_6H_5OPO_3Na_2$ and HCl in 100 ml ethanol) was added to speed the reaction, and the suspension was refluxed and stirred for 12 more days. The light blue solid, in an amount of 6.12 g, was separated by filtration. The X-ray powder diffraction pattern was characteristic of a layered material with a 14.6 Å layer spacing; lines of the form 00l were observed for l=1 to 6. The formula for the product appears to be:

$$VO(C_6H_5OPO_3) \cdot nS$$

where S is ethanol, water or mixtures of water and ethanol.

EXAMPLE 14

A total of 1.00 ml of concentrated HCl was added to a suspension of 3.28 g of 1-naphthylphosphate, monosodium salt in 50 ml of 95% ethanol. The mixture was stirred for one hour and sodium chloride was removed by filtration. The resulting 1-naphthylphosphoric acid solution was added to a suspension of 0.513 g of vanadium pentoxide in 75 mL of 95% ethanol, and the mixture was refluxed with stirring for 12 days. After cooling, a gray solid was separated from the red-brown supernatant by filtration, washed with ethanol, and suction dried to yield 1.97 g of product. An X-ray powder diffraction measurement revealed a sharp pattern which could be totally indexed ($>25$ lines) using an orthorhombic cell with $a=10.35$ Å, $b=14.85$ Å, and $c=9.60$ Å, the layer spacing corresponding to the b axis. The product had an overall formula of:

$$VO(C_{10}H_7OPO_3).nS$$

where S is ethanol, water or mixtures of water and ethanol.

The same compound was also prepared by heating 1-naphthylphosphonic acid with vanadyl sulfate in ethanol, using comparable amounts of reactants as were used above.

EXAMPLE 15

A total of 4.00 ml of concentrated HCl was added to a suspension of 8.00 g of barium 2-cyanoethylphosphate in 50 ml of 95% ethanol. The mixture was stirred for 0.5 hours and filtered to remove $BaCl_2$. The resulting 2-cyanoethylphosphoric acid solution was added to a suspension of 1.03 g of vanadium pentoxide in 75 ml of 95% ethanol. The mixture was refluxed with stirring for three days. After cooling to room temperature, a light blue solid was separated fron the blue supernatant by filtration, washed with ethanol, and suction dried to yield 1.99 g of product. The X-ray powder diffraction pattern showed a number of lines, including the first three in an 001 series corresponding to a layer spacing of 11.64 Å. The infrared spectrum contained an absorption at 2250 cm$^{-1}$ indicating retention of the cyano group. Elemental analysis indicated a formula of:

$$VO(NCCH_2CH_2OPO_3).2H_2O$$

(Found: 14.05%C. 2.80%H, 5.28%N; Calculated: 14.30%C, 3.20%H, 5.56%N).

This example illustrates another compound containing a pendant organic functional group (CN).

EXAMPLE 16

Vanadyl sulfate trihydrate (2.0 g) was added to a solution of 2.11 g of phenylarsonic acid in 100 ml of 95% ethanol. The resulting solution was heated at reflux for 4 days. After cooling, 0.52 g of a blue solid was separated by filtration from the deep blue filtrate. Powder X-ray diffraction data showed a single strong line at 10.2 Å typical of a layered compound with some disorder. Elemental analysis indicated a formula of:

$$VO(C_6H_5AsO_3).(3.6H_2O).(0.3C_2H_5OH)$$

(Found: 23.14%C, 3.45%H, 14.82%V, 21.67%As; Calculated: 22.94%C, 4.08%H, 14.74%V, 21.68%As).

EXAMPLE 17

Figure 5:
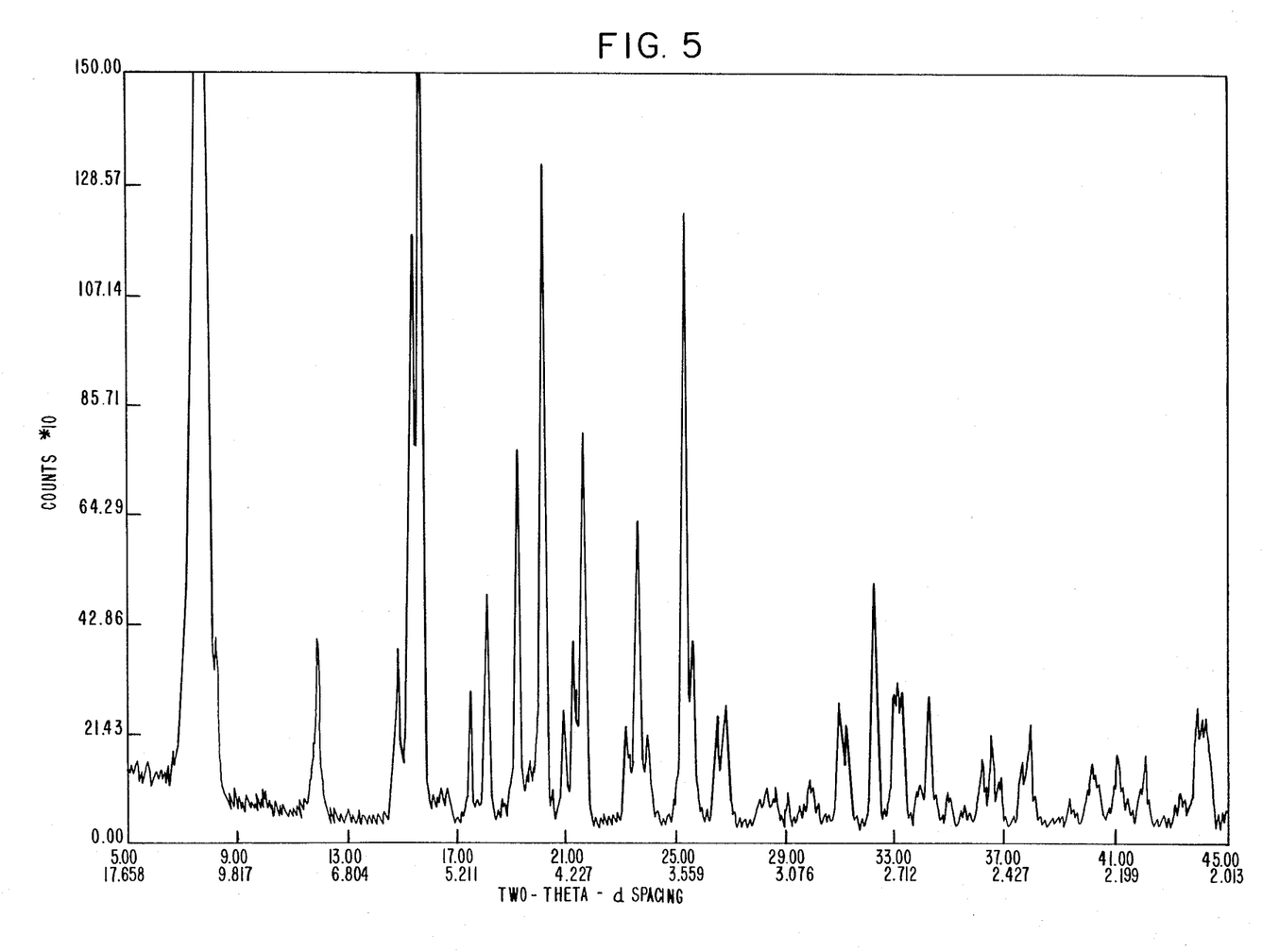
FIG. 5 represents an x-ray powder diffraction pattern for crystalline $VO(p-CH_3OC_6H_5PO_3).H_2O$ prepared as described in Example 17.

Vanadyl methoxyphenylphosphonate (VO(p-CH$_3$OC$_6$H$_4$PO$_3$).nS) containing both water and ethanol in the interlayer space was prepared as described in Example 4. The X-ray powder diffraction pattern of the product was indexed using an orthorhombic unit cell with $a=10.068$, $b=13.068$ and $c=9.894$ Å. The b axis determined the interlayer separation. The interlayer ethanol was removed from this phase by stirring in water for 16 hours. The product was filtered and dried under vacuum. The X-ray powder pattern of this product, shown in FIG. 5, which revealed that the compound remained crystalline, was indexed using an orthorhombic cell with cell constants $a=10.077$, $b=11.273$ and $c=9.77$ Å. The a and c axes were changed little but the interlayer separation (indicated by the b axis) contracted by 1.79 Å as a result of ethanol removal. On refluxing the water-containing product in ethanol, the b axis expanded, showing that ethanol was incorporated and that the water-ethanol exchange was reversible. This example illustrates that the compounds herein reversibly sorb molecules and thus are useful in separation processes as solid sorbents.

EXAMPLE 18

Figure 4:
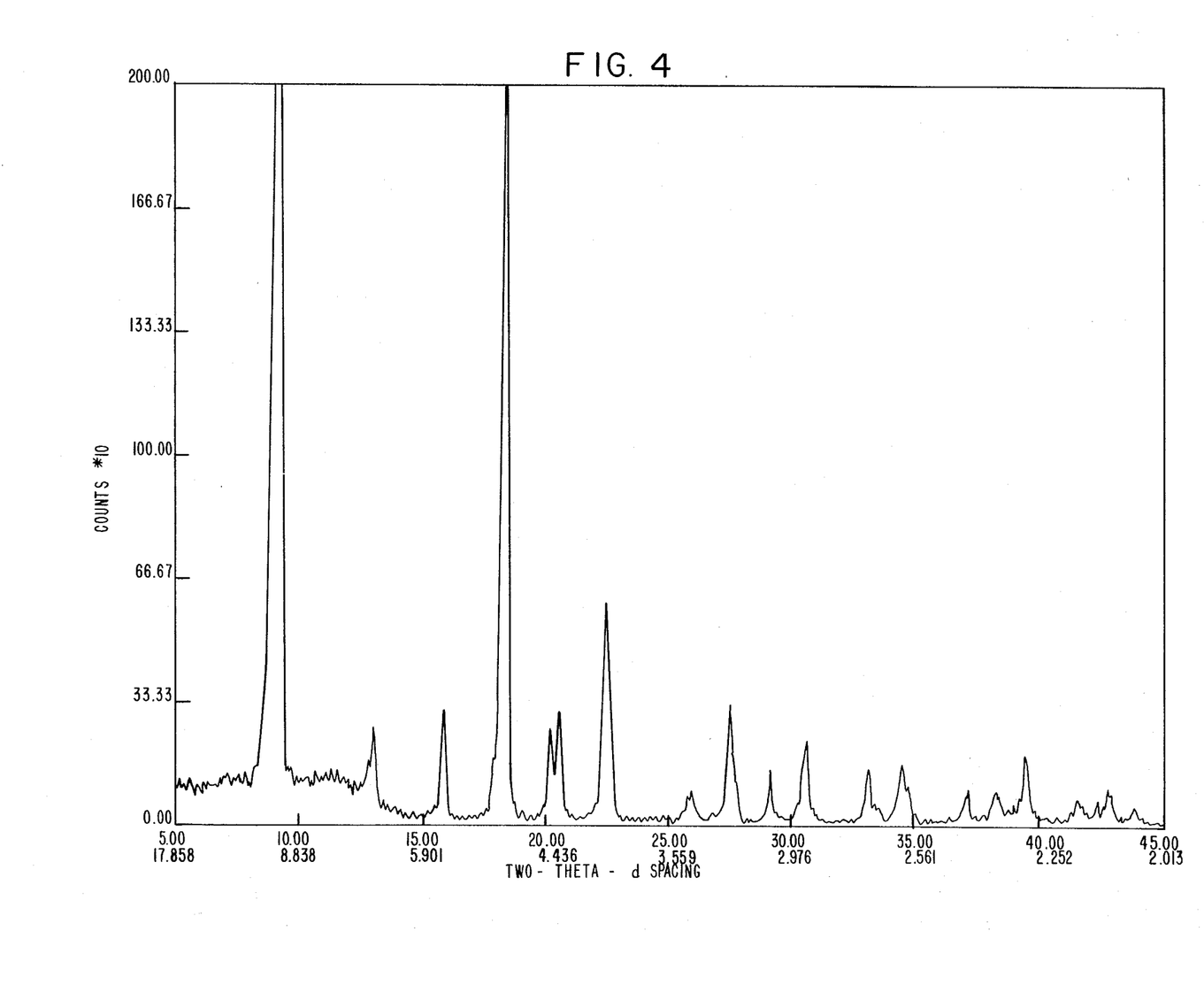
FIG. 4 represents an x-ray powder diffraction pattern for crystalline $VO(C_6H_5PO_3).H_2O$ prepared as described in Example 18.

Vanadyl phenylphosphonate (VO(C$_6$H$_5$PO$_3$).nS) containing both water and ethanol in the interlayer space was prepared as described in Example 1. The x-ray powder pattern was indexed using an orthorhombic unit cell with $a=10.005$, $b=12.115$ and $c=9.759$ Å. After water washing using the procedure described in Example 17, the crystalline product gave an X-ray pattern shown in FIG. 4 with orthorhombic unit cell dimensions $a=9.650$, $b=9.799$ and $c=572$ Å. The interlayer separation (b axis) contracts by 2.32 Å as a result of ethanol removal.

EXAMPLE 19

Examples 17 and 18 illustrate the reversible ethanol incorporation into the interlayer space of VOCH$_3$OC$_6$H$_4$PO$_3$.nS and VOC$_6$H$_4$PO$_3$.nS. Other alcohols, including straight chain aliphatic alcohols (C$_n$H$_{2n+1}$OH) and phenyl alcohols (C$_6$H$_5$(CH$_2$)$_n$OH) also intercalate both vanadyl phosphonates. Reactions were carried out by stirring the water-containing compounds with the alcohols for 16 hours at 60° C. The products were characterized by X-ray diffraction measurement of the interlayer expansion caused by alcohol intercalation. The layer spacing for VO(CH$_3$OC$_6$H$_4$PO$_3$) using C$_n$H$_{2n+1}$OH and C$_6$H$_5$(CH$_2$)$_{n-4}$OH and for VOC$_6$H$_5$PO$_3$ using C$_n$H$_{2n+1}$OH as a function of n is shown in FIG. 1.

EXAMPLE 20

A total of 0.6 g of vanadyl phenylphosphonate prepare as described in Example 1 and then washed with water (VO(C$_6$H$_5$PO$_3$).nH$_2$O) was stirred at room temperature for 16 hours in 25 ml of water containing 1600 ppm chloroform, 265 ppm benzene, and 1400 ppm 1-hexanol. After filtration the supernatant was analyzed by gas-solid chromatography and found to contain 300 ppm chloroform, 45 ppm benzene and 950 ppm 1-hexanol. Thus, 82% of the chloroform, 83% of the benzene and 31% of the 1-hexanol had been absorbed.

In summary, the present invention is seen to provide a class of novel compositions of matter which have a layered structure with pendant organic groups.

What is claimed is:

1. A solid composition of matter comprising layered oxides containing vanadium together with phosphorus or arsenic and a monovalent organic group, said layered compounds having one of the formulae:

$$VORAO_3 \cdot nS \text{ or } VOROAO_3 \cdot nS$$

where A is phosphorus or arsenic, S is a solvent molecule, R is an unsubstituted or alkyl-, alkoxy- or aryl-substituted alkyl or aryl group or a mixture thereof, and n is zero or a positive number, the layered compounds being characterized in that the vanadium has an average oxidation state in the range of 3.6 to 4.4 and is present in an amount such that the molar ratio of A:V ranges from, 0.8 to 1.2 throughout the oxide and the R groups are covalently bound to an A atom in the vanadium oxide layer directly through either carbon or oxygen.

2. The composition of claim 1 wherein A is phosphorus and S is ethanol.

3. The composition of claim 1 wherein A is phosphorus and S is ethanol, water or a mixture thereof.

4. The composition of claim 1 wherein R is selected from the group consisting of phenyl, biphenyl, $C_1$-$C_4$-alkyl or $C_1$-$C_4$-alkoxy-substituted phenyl, or $C_1$-$C_{20}$ alkyl groups, or mixtures thereof.

5. The composition of claim 1 wherein at least one R contains a functional group which is reactive with catalytically active metals.

6. The composition of claim 5 wherein the functional group contains a nitrogen, oxygen, phosphorus, sulfur or halogen atom.

7. The composition of claim 6 wherein the functional group is —COOR, —NH$_2$, —OH, —PR$_2$, —CN, —COOH, —SH or —SO$_3$H.

8. The composition of claim 6 wherein the functional group is —OH, —CN, —COOH or —COOR.

9. The composition of claim 1 wherein R is a mixture of alkyl or aryl groups.

10. The composition of claim 1 wherein n is from zero to 10.

11. The composition of claim 1 wherein the distance between layers is between about 8 and 80 Å.

12. A process for preparing the composition of claim 1 which comprises contacting a vanadium 5+ compound or 4+ compound with an effective amount of a phosphonic, phosphoric, arsonic or arsenic acid or mixture thereof substituted with said R group in the presence of a solvent when a vanadium 4+ compound is employed, and in the presence of a solvent and a reducing agent, if the solvent does not function as a reducing agent, when a vanadium 5+ compound is employed; heating the resultant mixture at temperatures ranging from about 50° C. to the reflux temperature of the reaction medium until the product is detected in isolable amounts; and recovering the product.

13. The process of claim 12 wherein the product is recovered by cooling and filtering the reaction mixture and then washing and drying the product.

14. The process of claim 12 wherein an R-substituted phosphonic, phosphoric or arsonic acid is employed and the solvent is an alcohol.

15. The process of claim 12 wherein an R-substituted phosphonic acid and vanadium pentoxide or vanadyl sulfate are contacted in ethanol and the heating temperature is the reflux temperature of the reaction medium.

16. The process of claim 15 wherein R is phenyl, biphenyl, $C_1$-$C_4$-alkyl- or $C_1$-$C_4$-alkoxy-substituted phenyl, or $C_1$-$C_{20}$ alkyl groups of mixtures thereof.

17. The process of claim 16 wherein at least one R contains a functional group which is reactive with catalytically active metals.

18. The process of claim 12 wherein more than one type of phosphonic, phosphoric, arsonic or arsenic acid is employed.

* * * * *